United States Patent
Ju et al.

(10) Patent No.: US 10,408,721 B2
(45) Date of Patent: Sep. 10, 2019

(54) APPARATUS FOR STRESS FREEZING EXPERIMENT DURING FRACTURING PROCESS

(71) Applicant: CHINA UNIVERSITY OF MINING AND TECHNOLOGY, BEIJING, Beijing (CN)

(72) Inventors: Yang Ju, Beijing (CN); Peng Liu, Beijing (CN); Hongbin Liu, Beijing (CN); Yongming Yang, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 0 days.

(21) Appl. No.: 16/313,469

(22) PCT Filed: Dec. 7, 2017

(86) PCT No.: PCT/CN2017/114951
§ 371 (c)(1),
(2) Date: Dec. 27, 2018

(87) PCT Pub. No.: WO2018/205584
PCT Pub. Date: Nov. 15, 2018

(65) Prior Publication Data
US 2019/0226958 A1 Jul. 25, 2019

(30) Foreign Application Priority Data

May 11, 2017 (CN) .......................... 2017 1 0329744

(51) Int. Cl.
*G01N 3/12* (2006.01)
*G01N 3/18* (2006.01)

(52) U.S. Cl.
CPC ................. *G01N 3/12* (2013.01); *G01N 3/18* (2013.01); *G01N 2203/0019* (2013.01);
(Continued)

(58) Field of Classification Search
CPC .... G01N 3/12; G01N 3/18; G01N 2203/0062; G01N 2203/0256; G01N 2203/0228;
(Continued)

(56) References Cited

U.S. PATENT DOCUMENTS 3,975,950 A    8/1976   Erdei

FOREIGN PATENT DOCUMENTS

CN    102607958 A    7/2012
CN    104655495 A    5/2015
(Continued)

OTHER PUBLICATIONS

Ju et al., "Visualization of the complex structure and stress field inside rock by means of 3D printing technology", Chin. Sci. Bull., 59 (36): 5354-5365 (Year: 2014).*
(Continued)

*Primary Examiner* — Nathaniel T Woodward
(74) *Attorney, Agent, or Firm* — Yue (Robert) Xu; Apex Attorneys at Law, LLP

(57) ABSTRACT

A device for stress-freezing experiments during fracturing process according to the present application, in which heating and cooling treatment on a specimen under corresponding temperature control according to a preset temperature gradient and a photosensitive curve is performed by a temperature control system, to realize stress-freezing of the specimen; a pressure is applied to a specimen by a true triaxial servo loading system; and corresponding fracturing experiments are performed to the specimen by a fracturing liquid pumping system having an output end arranged in a thermo-controlled oven.

9 Claims, 9 Drawing Sheets

(52) U.S. Cl.
CPC ............... *G01N 2203/0048* (2013.01); *G01N 2203/0062* (2013.01); *G01N 2203/026* (2013.01); *G01N 2203/0226* (2013.01); *G01N 2203/0228* (2013.01); *G01N 2203/0256* (2013.01)

(58) Field of Classification Search
CPC ... G01N 2203/0226; G01N 2203/0048; G01N 2203/0019; G01N 2203/026
USPC ........................................................... 73/799
See application file for complete search history.

(56) References Cited

FOREIGN PATENT DOCUMENTS

| | | | |
|---|---|---|---|
| CN | 104655495 U | * | 5/2015 |
| CN | 204881966 U | | 12/2015 |
| CN | 105608736 A | | 5/2016 |
| CN | 206020193 A | * | 3/2017 |
| CN | 206020193 U | | 3/2017 |
| CN | 106644734 A | | 5/2017 |
| JP | H07198582 A | | 8/1995 |

OTHER PUBLICATIONS

International Search Report for PCT/CN2017/114951 dated Feb. 26, 2018, ISA/CN.

Ju, Yang et al.,Visualization of the Complex Structure and Stress Field Inside Rock by Means of 3D Printing Technology, Chinese Science Bulletin, Nov. 30, 2014 (Nov. 30, 2014) , 59(32), ISSN: 0023-074X, pp. 3109-3119.

* cited by examiner

APPARATUS FOR STRESS FREEZING EXPERIMENT DURING FRACTURING PROCESS

This application is the national phase of International Application No. PCT/CN2017/114951, titled "APPARATUS FOR STRESS FREEZING EXPERIMENT DURING FRACTURING PROCESS", filed on Dec. 7, 2017, which claims the priority to Chinese Patent Application No. 201710329744.1 titled "DEVICE FOR STRESS-FREEZING EXPERIMENTS DURING FRACTURING PROCESS", filed with the Chinese State Intellectual Property Office on May 11, 2017, the entire disclosures of which are incorporated herein by reference.

FIELD

The present application relates to the stress-freezing technical field, and particularly relates to a device for stress-freezing experiments during fracturing process.

BACKGROUND

Presently, the crack evolution law in a fracturing process of unconventional reservoir rock media is a "black box" problem. Therefore, the existing laboratory researches on the fracturing process of fracturing media of various phase states mostly focus on qualitative analyses of distribution characteristics of a crack network formed after fracturing, and an evolution process of the stress field which plays a decisive role in the initiation and propagation of the fracturing crack network is difficult to be visually displayed and accurately described.

In the conventional technology, the numerical simulation method is also used to quantitatively analyze the distribution and evolution law of the stress field in the crack propagation process. However, it is worth noting that a series of issues such as geometric model, boundary conditions, mesh model, unit contact and separation, material parameters, constitutive relations, fracture and damage criteria are required to be simplified in the numerical simulation. The simplified process and issues such as computational scale and computational efficiency may all significantly affect the computational accuracy of the fracturing stress field. In particular, due to limitation of experimental methods and test conditions, most numerical simulation results lack experimental verification, thus the accuracy and reliability of the numerical analysis remains widely controversial, and the numerical analysis is difficult to be directly applied on an engineering site.

Therefore, an experimental device is urgently to be provided presently, to realize visualization and transparent display of the evolution law of global stress field during complex crack network initiation and propagation in the fracturing process.

SUMMARY

A device for stress-freezing experiments during fracturing process is provided according to the present application in order to realize visualization and transparent display of the evolution law of global stress field during complex crack network initiation and propagation in the fracturing process.

In order to achieve the above object, the technical solutions according to the present application are provided hereinafter.

A device for stress-freezing experiments during fracturing process includes:

a temperature control system, which includes a thermo-controlled oven and is configured to perform heating and cooling treatment on a specimen arranged in the thermo-controlled oven according to a preset temperature gradient and a photosensitive curve, to realize stress-freezing experiment to the specimen; wherein the specimen is a transparent photosensitive model printed by a 3D printer, and the photosensitive curve is a photosensitive curve of the photosensitive model;

a true triaxial servo loading system configured to apply a pressure to the specimen; and a fracturing fluid pumping system having an output end arranged in the thermo-controlled oven and being configured to perform a corresponding fracturing experiment on the specimen.

Preferably, the thermo-controlled oven includes a multi-hole cover plate, a sealing assembly and five thermo-controlled oven walls; wherein the multi-hole cover plate and the five thermo-controlled oven walls are each provided with a piston rod inlet; and the multi-hole cover plate is provided with two circulating air inlets.

Preferably, the temperature control system further includes a heat source control system, a direct heating unit, an ambient heating unit, a cooling control system, a cooling unit and a temperature detecting unit; wherein the heat source control system is configured to control the operations of the direct heating unit and the ambient heating unit; and the cooling control system is configured to control the operation of the cooling unit.

Preferably, the direct heating unit includes six electric heating tubes and six heating back plates;

the ambient heating unit includes an air heater;

the cooling unit includes six cooling tubes;

the temperature detecting unit includes at least six temperature sensors;

each of the electric heating tubes is arranged in the respective heating back plate, to perform main temperature rising treatment in various directions of the specimen through direct heating or directly cool the specimen by injecting a cooling liquid;

the air heater is configured to perform temperature rising compensation to the specimen by increasing an ambient temperature;

the temperature sensors are respectively arranged in both the thermo-controlled oven and pressing plates of the true triaxial servo loading system;

one side of each of the heating back plates is connected to a self-adaptive loading device, and another side of each of the heating back plates is attached to one of the pressing plates;

the cooling control system is configured to control the injection of the cooling liquid or a cooling gas in the cooling tubes; and each of the cooling tubes is arranged at an inner side of the thermo-controlled oven wall.

Preferably, the true triaxial servo loading system includes a beam-column frame, five sets of servo actuators, five sets of servo distributors, a set of servo oil source, a set of servo motion control system, hydraulic system accessories, a self-adaptive series stress sensor, a displacement sensor and a specimen fixing and positioning unit; wherein the specimen fixing and positioning unit is arranged at a bottom of the thermo-controlled oven;

the beam-column frame is configured for supporting and to allow piston rods, the multi-hole cover plate and the specimen fixing and positioning unit to realize controllable movement;

the output of the servo motion control system controls the corresponding servo actuator to motion through the respective servo distributor;

the five sets of servo actuators apply pressure on a top of the specimen and in horizontal directions of the specimen by corresponding piston rods and pressing plates respectively;

the servo oil source and the hydraulic system accessories are used to push the corresponding piston rods by the five sets of servo actuators;

the self-adaptive series stress sensor is configured to measure stresses applied on the specimen in various directions; and the displacement sensor is configured to measure displacements of the specimen in various directions.

Preferably, the self-adaptive series stress sensor includes a large-range pressure sensor, a small-range pressure sensor, a mounting sleeve, a thrust plate and an elastomer; wherein the small-range pressure sensor is arranged in the mounting sleeve;

the elastomer is arranged between a bottom of the mounting sleeve and the small-range pressure sensor;

a deformation gap of the elastomer is set between the thrust plate and a top of the mounting sleeve;

the small-range pressure sensor is configured to detect a pressure applied by the thrust plate; and the large-range pressure sensor is configured to detect a pressure applied by the mounting sleeve.

Preferably, the device for stress-freezing experiments during fracturing process further includes a specimen automatic fixing and positioning unit, which includes four orienting guide rails, a specimen mounting platform, a fixture and a top servo actuator; the specimen mounting platform slides along the four orienting guide rails, and motions in linkage with the top servo actuator to achieve the lifting mounting and accurate positioning of the specimen.

Preferably, the device for stress-freezing experiments during fracturing process further includes a self-adaptive loading device arranged between the heating back plates and the piston rods, wherein the self-adaptive loading device is in contact with the piston rods, and is configured to eliminate shear stresses on surfaces of the specimen; and the heating back plate is connected to a sliding assembly.

Preferably, the self-adaptive loading device includes four self-adaptive loading plates for horizontal direction and two self-adaptive floating platforms for upper and lower surfaces; wherein the self-adaptive loading plate for horizontal direction includes a fixed plate, a sliding plate and a sliding module, the sliding module is arranged between the fixed plate and the sliding plate, and includes multiple rows of roller chains corresponding to a horizontal displacement;

the self-adaptive floating platform for upper and lower surfaces includes a fixed plate, two sliding plates and two sliding modules, wherein one sliding module is arranged between the fixed plate and one sliding plate, another sliding module is arranged between the two sliding plates, and the two sliding modules respectively includes multiple rows of roller chains corresponding to each of displacements in two orthometric directions in a horizontal plane.

Preferably, the fracturing fluid pumping system is a constant temperature and pressure pumping system of supercritical $CO_2$.

Preferably, the constant temperature and pressure pumping system of supercritical $CO_2$ includes a $CO_2$ cylinder, a temperature-control thermostatic bath, a constant speed and pressure pump, a three-way injection valve, two vent valves and two pressure sensors; wherein the $CO_2$ cylinder is connected to the temperature-control thermostatic bath through a filter;

the temperature-control thermostatic bath is connected to an input end of the three-way injection valve through the constant speed and pressure pump;

an output end of the three-way injection valve is connected to a quick joint, to function as an output end of the constant temperature and pressure pumping system of supercritical $CO_2$;

the two pressure sensors are arranged in the temperature-control thermostatic bath and the constant speed and pressure pump respectively; and the two vent valves are arranged in the temperature-control thermostatic bath and the constant speed and pressure pump respectively.

In the device for stress-freezing experiments during fracturing process according to the present application, corresponding heating and cooling treatment is performed on a specimen according to a preset temperature gradient and a photosensitive curve by a temperature control system, to realize stress-freezing of the specimen; corresponding pressures are applied to a specimen by a true triaxial servo loading system; and corresponding fracturing experiments are performed to the specimen based on a fracturing liquid pumping system having an output end arranged in a thermo-controlled oven. Since the specimen is a transparent photosensitive model printed by a 3D printer, by incorporating the stress loading with the true triaxial servo loading system, stress-freezing experiment under the accurate temperature control of the temperature control system, and the fracturing experiment by the fracturing liquid pumping system, visualization and transparent display of the evolution law of global stress field of a crack tip during complex crack network initiation and propagation in the fracturing process can be realized.

BRIEF DESCRIPTION OF THE DRAWINGS

For more clearly illustrating embodiments of the present application or the technical solutions in the conventional technology, drawings referred to describe the embodiments or the conventional technology will be briefly described hereinafter. Apparently, the drawings in the following description are only some examples of the present application, and for those skilled in the art, other drawings may be obtained based on these drawings without any creative efforts.

DETAIL DESCRIPTION

The technical solution according to the embodiments of the present application will be described clearly and completely as follows in conjunction with the accompany drawings in the embodiments of the present application. It is obvious that the described embodiments are only a part of the embodiments according to the present application, rather than all of the embodiments. All the other embodiments obtained by those skilled in the art based on the embodiments in the present application without any creative work belong to the scope of protection of the present application.

A device for stress-freezing experiments during fracturing process is provided according to the present application in order to realize visualization and transparent display of the evolution law of global stress field during complex crack network initiation and propagation in the fracturing process.

Figure 1:
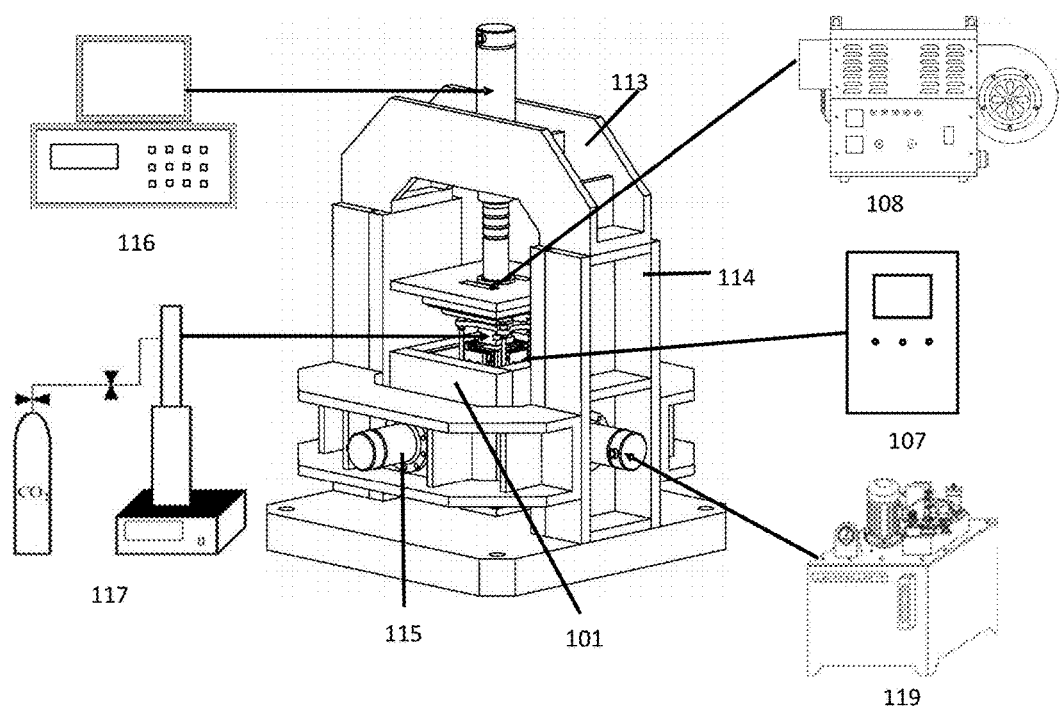
FIG. 1 is a schematic view showing the structure of a device for stress-freezing experiments during fracturing process according to an embodiment of the present application.

As shown in FIG. 1, the device for stress-freezing experiments during fracturing process includes:

a temperature control system, which includes a thermo-controlled oven 101 and is configured to perform heating and cooling treatment on a specimen 109 arranged in the thermo-controlled oven 101 according to a preset temperature gradient and a photosensitive curve, to realize stress-freezing on the specimen 109, where the specimen 109 is a transparent photosensitive model printed by a 3D printer;

a true triaxial servo loading system configured to apply pressure to the specimen 109, which can apply compressive stresses mutually different in three directions for the specimen 109, to simulate a true stress state of the deeply-buried low-permeability reservoir rock; and a fracturing fluid pumping system 117 having an output end arranged in the thermo-controlled oven 101 and configured to perform a corresponding fracturing experiment on the specimen 109.

The specific operation principle is as follows.

In order to simulate the three-dimensional stress condition of deeply-buried low permeability reservoirs, to simulate a true triaxial stress state and ensure the accuracy of fracturing experiments, the true triaxial servo loading system, for example, a triaxial hydraulic servo loading system, is required to be arranged in the thermo-controlled oven 101 which can control the temperature with a high precision.

In order to realize the visualization and transparent display of the evolution law of global stress field during complex crack network initiation and propagation in a fracturing process, the applicant proposes that a stress-freezing experiment during the fracturing process can be performed to the photosensitive model obtained by 3D printing based on a fracturing device.

However, the stress-freezing experiment is very sensitive to the freezing temperature and stress conditions. The existing fracturing device cannot meet the requirements of the stress-freezing experiment both in temperature control method and triaxial loading accuracy.

In order to complete the stress-freezing experiment, accurate temperature rising and lowering control is required. The photosensitive model manufactured by 3D printing is different from the conventional rock materials, and is more sensitive to the temperature. Therefore, in order to realize the stress-freezing experiment, the temperature rising and lowering control should be more accurate. In a specific practical application, in order to realize stress-freezing of the specimen 109, the temperature control system would heat and cool the specimen 109 according to a preset temperature gradient and the photosensitive curve of the photosensitive model.

Specifically, in the heating process, the accurate control of the temperature condition of the specimen 109 can be guaranteed by combining direct heating and ambient temperature; a uniform hot air circulation system provides an ambient temperature for the cubic specimen 109 with a size of 100×100×100 mm, so that the temperature uniformity in the thermo-controlled oven 101 is ±3%.

Figure 2:
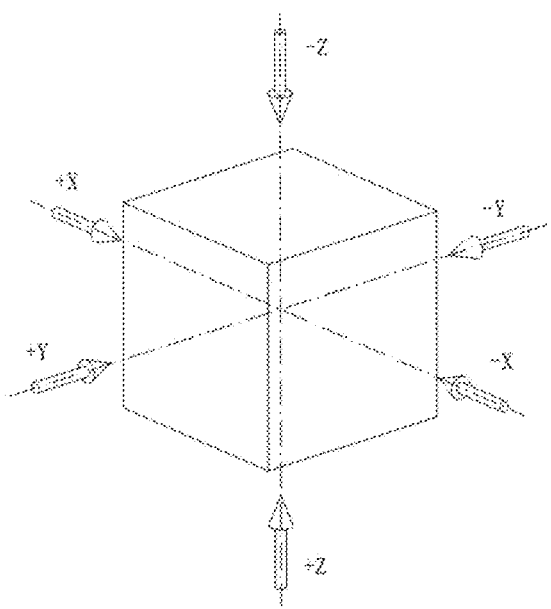
FIG. 2 is a schematic view showing a loading direction of a true triaxial servo loading system according to the embodiment of the present application.

During a true triaxial loading process of the true triaxial servo loading system in the experiment, the high-accuracy servo loading can be applied to the specimen 109 in five directions of +x, −x, +y, −y, +z as shown in FIG. 2. The loading system in each of the directions can be operated independently, or can be controlled by a program to perform multi-channel coordinated continuous work. Specifically, the triaxial pressure ranges are that: 0 to 30 MPa in x and y directions (bidirectional loading), with a stroke being 50 mm; 0 to 50 MPa in z direction (one-way loading), with a stroke being 300 mm; the loading accuracy is smaller than or equal to ±0.05% F.S; and the displacement control accuracy is ±0.02. Meanwhile, high-accuracy stress and displacement measurement devices can be provided in six directions of +x, −x, +y, −y, +z, −z, to accurately measure and feedback the stress and displacement in three directions, and a deformation of the specimen 109 is automatically calculated by program. The measurement accuracy in x, y, and z directions under different measuring ranges can reach ±0.1% F.S.

In the device for stress-freezing experiments during fracturing process provided in this embodiment, since the specimen 109 is a transparent photosensitive model printed by the 3D printer, a stress-freezing model with real crack structure is manufactured by 3D printing technology. With the combination of the stress loading by the true triaxial servo loading system, stress-freezing experiment under the accurate temperature control of the temperature control system, and the fracturing experiment by the fracturing liquid pumping system 117, visualization and transparent display of the evolution law of global stress field of complex crack network initiation and propagation in the fracturing process can be realized.

Figure 3:
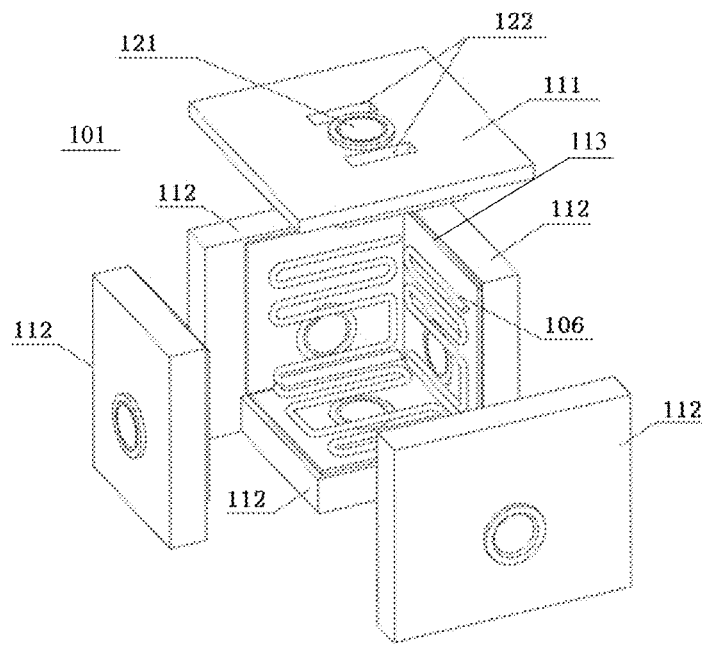
FIG. 3 is a schematic view showing the structure of a thermo-controlled oven according to the embodiment of the present application.

As shown in FIG. 3, the thermo-controlled oven 101 includes a multi-hole cover plate 111, a sealing assembly 113 and five thermo-controlled oven walls 112; wherein the multi-hole cover plate 111 and the five thermo-controlled oven walls 112 are each provided with an inlet 121 for a piston rod 118; and the multi-hole cover plate 111 is provided with two circulating air inlets 122.

Figure 4:
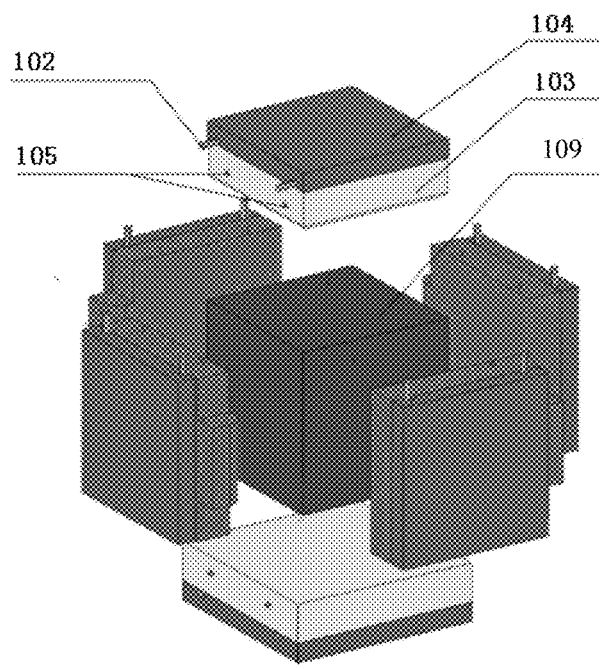
FIG. 4 is a schematic view showing a partial structure of a temperature control system according to the embodiment of the present application.
Figure 5:
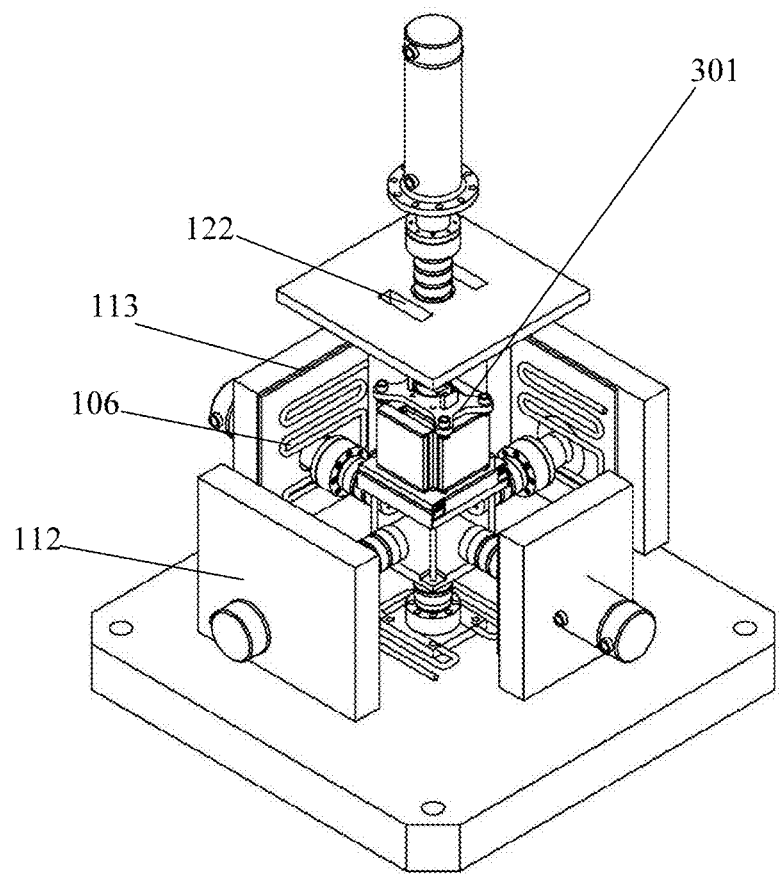
FIG. 5 is a schematic view showing the structure of the true triaxial servo loading system according to the embodiment of the present application.

As shown in FIGS. 1, 3 and 4, the temperature control system includes a thermo-controlled oven 101, a heat source control system 107, six electric heating tubes 102, an air heater 108, six pressing plates 103, six heating back plates 104, at least six temperature sensors 105, a cooling control system and six cooling tubes 106. Wherein, the six electric heating tubes 102 and six heating back plates 104 belong to direct heating unit;

the air heater 108 belongs to an ambient heating unit;

the six cooling tubes 106 belong to a cooling unit;

the at least six temperature sensors 105 belong to a temperature detecting unit;

the heat source control system 107 is configured to control the operation of the electric heating tubes 102 and the air heater 108;

each of the electric heating tubes 102 is arranged in the respective heating back plate 104, and is configured to perform main temperature rising treatment to the specimen 109 in various directions through direct heating;

the temperature sensors 105 are respectively arranged in both the thermo-controlled oven 101 and the pressing plates 103 of the true triaxial servo loading system;

the air heater 108 is configured to perform temperature rising compensation on the specimen 109 by increasing an ambient temperature;

the cooling control system is configured to control the injection of the cooling liquid or a cooling gas in the cooling tubes 106; and each of the cooling tubes 106 is arranged at an inner side of the thermo-controlled oven wall 112, as shown in FIG. 3.

Preferably, each of the pressing plates 103 and the heating back plates 104 has a square shape with a side length of 100 mm.

Specifically, the control accuracy of the electric heating tube 102 is controlled within 0.1° C., and the accuracy of the temperature sensor can reach ±0.1° C.

Considering that the traditional thermo-controlled oven 101 is affected by various factors such as air inlet, air outlet, grille, and sharp corners in the thermo-controlled oven, the temperature inside the thermo-controlled oven is difficult to maintain uniform. To solve this problem, the present embodiment directly heats the specimen 109 using steel plates, i.e., the pressing plates 103 which contacts with the specimen 109, thus ensuring that the heat can be uniformly diffused and conducted into the specimen. The temperature sensors 105 are arranged inside the steel plates at six sides, which can sense the temperature change of the pressing plates 103 in time, and the temperature difference change can be controlled within 1° C. through a multi-channel heat source control system 107 in which each channel is controlled by 16 sets of independent PID control manners.

In order to ensure stable and reliable temperature control, the specimen 109, pressing heads in contact with surfaces of the specimen (including the heating back plates 104 and the pressing plates 103), and part of the piston rods 118 of a servo cylinder are arranged in a thermo-controlled oven 101 controlled to have a constant temperature; side walls, a bottom plate and a top cover plate of the thermo-controlled oven 101 are processed separately, and finally supported and connected by a rigid frame.

In order to rise the temperature, an independent heating system is provided in the pressing heads which are in direct contact with six surfaces of the specimen 109, to directly heat the specimen 109. A temperature generated by the heat source may be slightly lower than a target temperature of the specimen 109, and this temperature difference is compensated by controlling the air heater 108 to raise the ambient temperature in the thermo-controlled oven 101. Meanwhile, temperature sensors 105 are arranged in the six pressing heads, specifically in the pressing plates 103, to directly monitor and comprehensively evaluate the temperature of the surfaces of the specimen 109, thus the temperature data of the surfaces of the specimen 109 are feedback efficiently and accurately to control the operation of the heating system. According to the principle of circulating air flow in the thermo-controlled oven 101, two circulating air inlets 122 are provided in the multi-hole cover plate 111 at a top of the thermo-controlled oven 101, so that a circulating hot air system is formed in the thermo-controlled oven, thereby ensuring the uniformity of the ambient temperature inside the thermo-controlled oven. A temperature sensor should also be provided in the thermo-controlled oven to monitor the ambient temperature in the thermo-controlled oven 101 at the same time, thus the heating and cooling processes of the specimen 109 can be controlled in coordination with the temperature data in the pressing heads.

In order to realize the temperature lowering treatment, stainless steel tubes, i.e., the cooling tubes 106 shown in FIG. 3 are uniformly distributed on the side walls of the thermo-controlled oven 101, and the temperature in the thermo-controlled oven 101 can be lowered by uniformly injecting a cooling liquid or blowing circulating cold air into the tubes in conjunction with a circulating air system inside the thermo-controlled oven 101. In addition, the cooling liquid may also be injected into the electric heating tubes 102 to directly cool the specimen. Since the temperature and a blowing speed of the cold air can be accurately controlled, the temperature lowering process of the specimen 109 can be accurately controlled in terms of the temperature data of the temperature sensors in the pressing heads and the thermo-controlled oven 101.

The rest operation principle is the same as the above embodiment, and will not be described again herein.

As shown in FIG. 1, the true triaxial servo loading system includes a beam frame 113, a column frame 114, five sets of servo actuators 115, five sets of servo distributors 116, a set of servo oil source 119, a set of servo motion control system 116, hydraulic system accessories, a self-adaptive series stress sensor 20, a displacement sensor and a specimen fixing and positioning unit 301; wherein the specimen 109 fixing and positioning unit is arranged at a bottom of the thermo-controlled oven 101;

the beam frame 113 and the column frame 114 are configured to support the piston rods 118, the multi-hole cover plate 111 and the specimen 109 fixing and positioning unit and allow the same to realize controllable movement;

the output of the servo motion control system 116 controls the corresponding servo actuator 115 to motion through the respective servo distributor 116;

the five sets of servo actuators 115 apply pressures on the top of the specimen 109 and in horizontal directions of the specimen 109 by corresponding piston rods 118 and pressing plates respectively;

the servo oil source 119 and the hydraulic system accessories are used to push the corresponding piston rods 118 by the five sets of servo actuators 115.

The true triaxial servo loading system further includes a self-adaptive series stress sensor 20 configured to measure stresses applied to the specimen 109 in various directions, and a displacement sensor configured to measure displacements of the specimen 109 in various directions.

Figure 6:
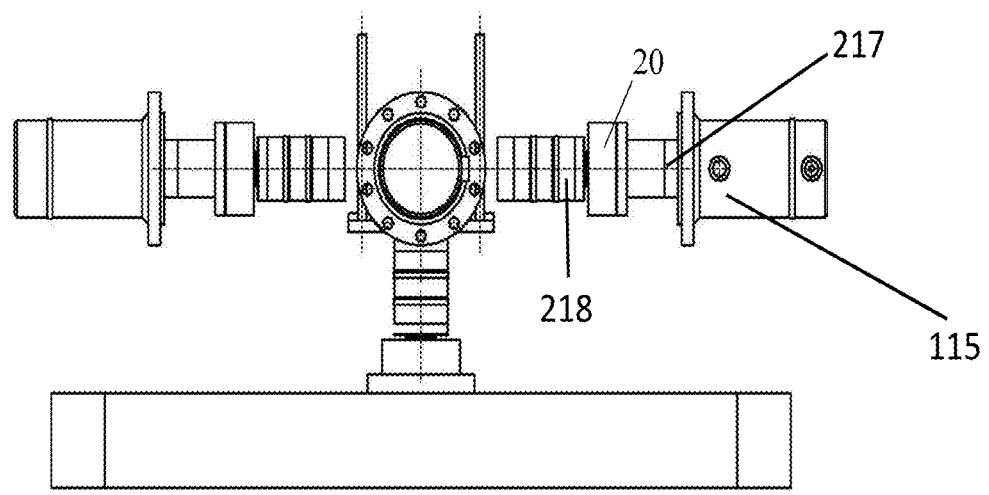
FIG. 6 is a top view showing the true triaxial servo loading system.

As shown in FIG. 6, the self-adaptive series stress sensor 20 is mounted between a servo pressing rod 217 and a thermal insulation layer 218.

Figure 7:
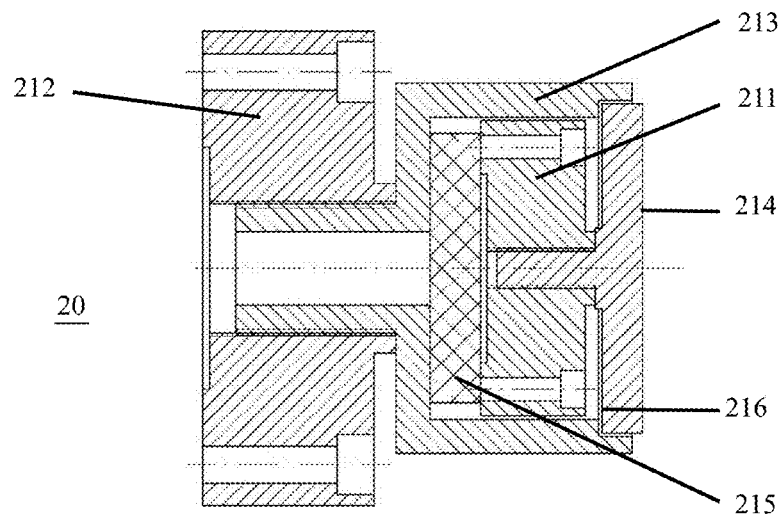
FIG. 7 is a schematic view showing the structure of a self-adaptive series stress sensor according to the embodiment of the present application.

As shown in FIG. 7, the self-adaptive series stress sensor 20 includes a large-range pressure sensor 211, a small-range pressure sensor 212, a mounting sleeve 213, a thrust plate 214 and an elastomer 215. The small-range pressure sensor 212 is arranged in the mounting sleeve 213. The elastomer 215 is arranged between a bottom of the mounting sleeve 213 and the small-range pressure sensor 212. A deformation gap for the elastomer 215 is set between the thrust plate 214 and a top of the mounting sleeve 213. The small-range pressure sensor 212 is configured to detect a pressure applied by the thrust plate 214, and the large-range pressure sensor 211 is configured to detect a pressure applied by the mounting sleeve 213.

The hydraulic servo loading device is designed to have a pressure capacity of 300 KN in two horizontal directions, and two opposite hydraulic cylinders are arranged in one loading direction. The designed pressure capacity in a vertical direction is 500 KN, a manner of fixing the bottom and servo loading at the top is employed, and the loading accuracy can reach ±0.05% F.S. The pressure sensors collect and feedback the stress values applied to the specimen 109.

Figure 8:
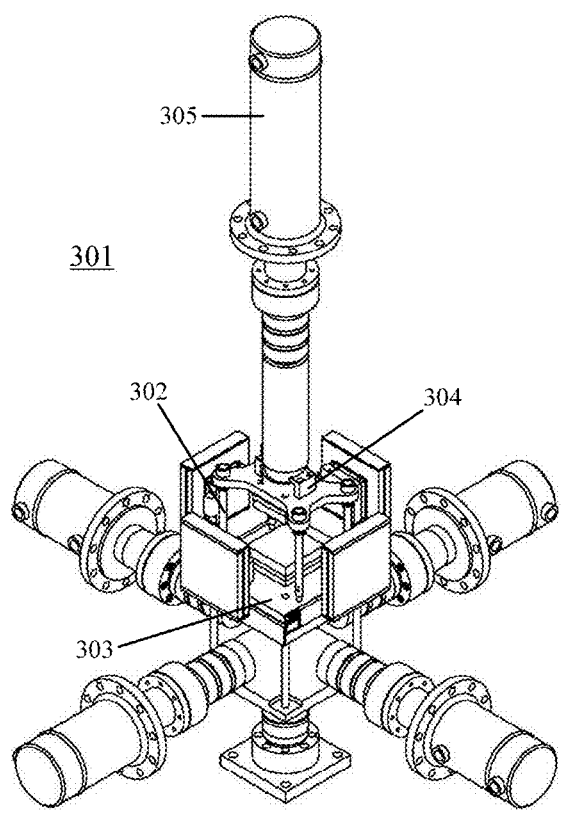
FIG. 8 is a schematic view showing the structure of a specimen automatic fixing and positioning unit according to the embodiment of the present application.

Since the loading system and the temperature control system are closed systems, in order to fix and position of the specimen 109 accurately, the device for stress-freezing experiments during fracturing process is further provided with a specimen automatic fixing and positioning unit 301. As shown in FIG. 8, the specimen automatic fixing and positioning unit 301 includes four orienting guide rails 302, a specimen mounting platform 303, a fixture 304 and a top servo actuator 305. The specimen mounting platform 303 slides along the four orienting guide rails 302, and moves in linkage with the top servo actuator 305 to lift and position the specimen 109 accurately. In order to position the specimen 109 accurately in the thermo-controlled oven 101, a top plate of the thermo-controlled oven 101 can be raised and lowered along with the pressing rod in the vertical direction, to open and close the thermo-controlled oven 101. A liftable platform with a good rigidity is provided below the vertical pressing rod to fix the specimen 109. The specimen 109 descends with the platform, and is accurately positioned at a central position of four horizontal hydraulic servo loading rods, thus the specimen 109 is positioned in the triaxial loading system, and the specimen 109 is fixed by the specimen 109 fixing and positioning unit.

Since the pressure sensor may generate a certain linearity error under different measuring ranges, a multi-section pressure sensor is employed in this embodiment to minimize the linearity error. In the conventional triaxial loading experiment, in order to make the pressure plate 103 and the specimen 109 closely fit, and make the specimen 109 in position, the specimen 109 is pre-stressed before the target pressure is applied. However, the mechanical properties of the 3D printed model used in the fracturing experiment and the stress-freezing experiment are somewhat different from those of the real rock materials, especially in the stress-freezing experiment, the target pressure of 10 KN or lower may be chosen, and an excessive initial pre-stress may have a great effect on the experimental results. Therefore, in order to improve the accuracy of the experiment, it is necessary to ensure that the initial pre-stress applied during each experiment is extremely small. According to the results of multiple repeated stress-freezing experiments, a preferable initial applied pressure should be controlled within 2 KN. In addition, the pressure sensor selected according to the limit pressure value is a very rigid elastomer, and the sensor of this measuring range has a low recognition accuracy for the force of 2 KN, which brings difficulty to the control of the initial loading accuracy of the specimen 109. Therefore, in order to solve this problem, in this embodiment, a small-range pressure sensor is connected to a large-range pressure sensor in series, and the small-range sensor is overload-protected by a mechanical structure, and then the data acquisition of the large-range and small-range sensors is automatically switched by a control program.

Specifically, when a load below 2 KN is applied, the force is transmitted to the large-range pressure sensor 211 through the small-range pressure sensor 212, the elastomer 215 and the mounting sleeve 213, but the program reads data from the 2 KN small-range pressure sensor 212. When the load is gradually increased, the elastomer 215 starts to deform. When the load reaches 2 KN, the deformation gap 216 of the elastomer 215 disappears, and the small-range pressure sensor 212 is no longer compressed to deform, thus avoiding the damage of the small-range pressure sensor 212. And the applied loading at this moment is directly transmitted to the large-range pressure sensor 211 through the mounting sleeve 213. At this time, the program automatically switches to read data from the large-range pressure sensor 211. Namely, with the self-adaptive series stress sensor in this embodiment, not only the problem that a small load cannot be distinguished is solved, but also the specimen 109 is automatically aligned.

The device for stress-freezing experiments during fracturing process further includes a self-adaptive loading device 21.

Figure 9:
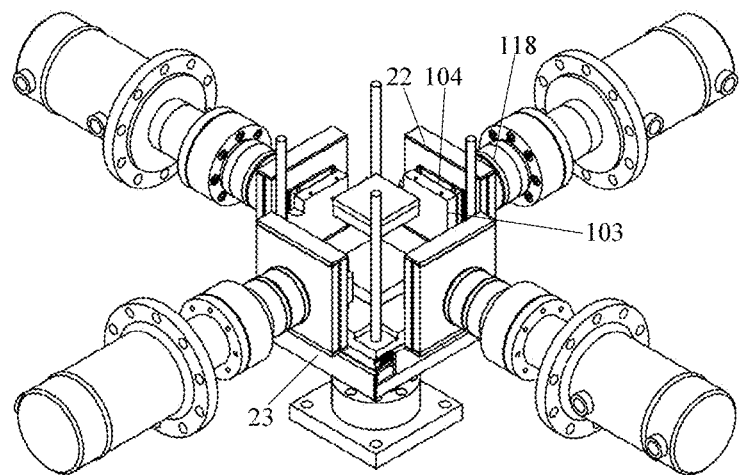
FIG. 9 is a schematic view showing the connection of a self-adaptive loading device with heating back plates and piston rods according to the embodiment of the present application.

As shown in FIG. 9, the self-adaptive loading device 21 is arranged between the heating back plates 104 and the piston rods 118, and is in contact with the piston rods 118, to eliminate shear stresses on the surfaces of the specimen 109; and a pressing plate 103 is fitted on another side of each of the heating back plates 104.

Figure 10:
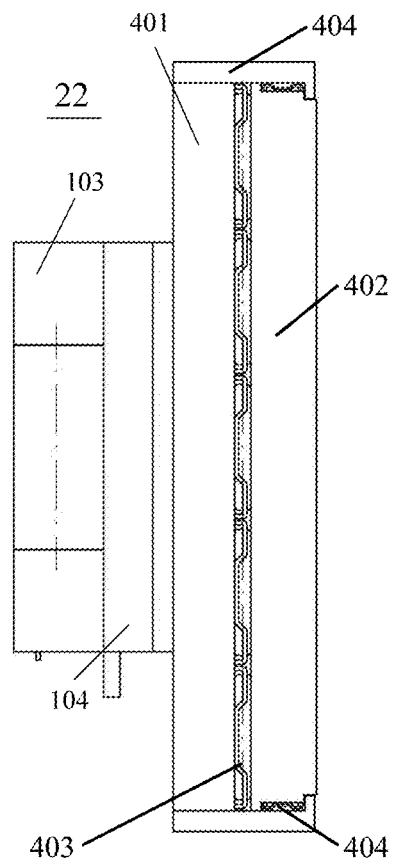
FIG. 10 is a schematic view showing the structure of a self-adaptive loading plate for horizontal direction according to the embodiment of the present application.
Figure 12:
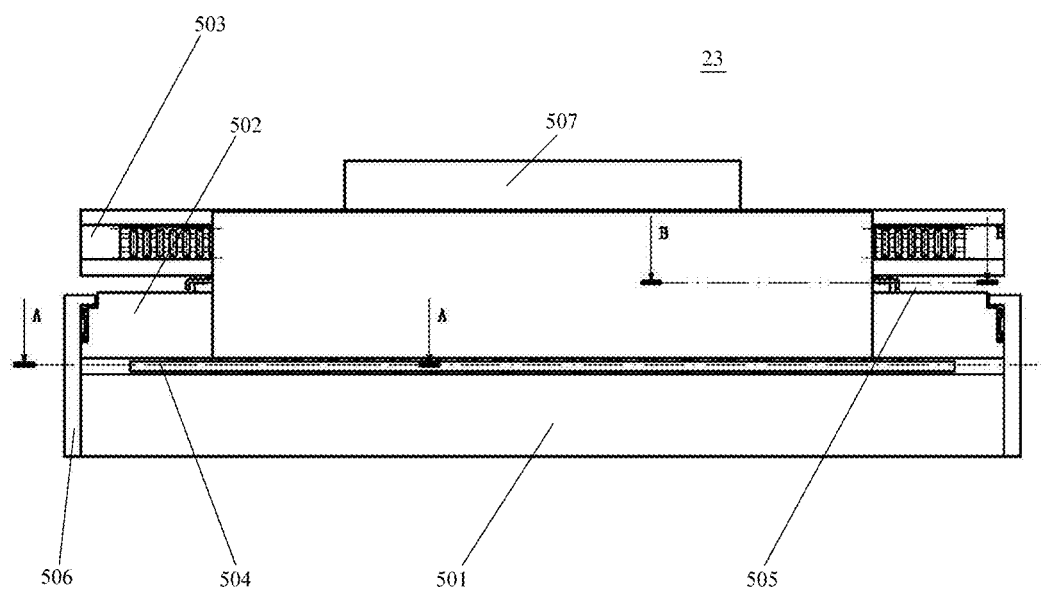
FIG. 12 is a schematic view showing the structure of a self-adaptive floating platform for upper and lower surfaces according to the embodiment of the present application.
Figure 13:
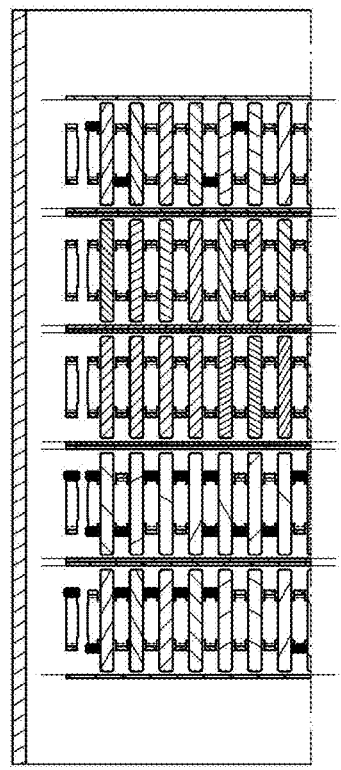
FIG. 13 is a sectional view showing A-A in FIG. 12.
Figure 14:
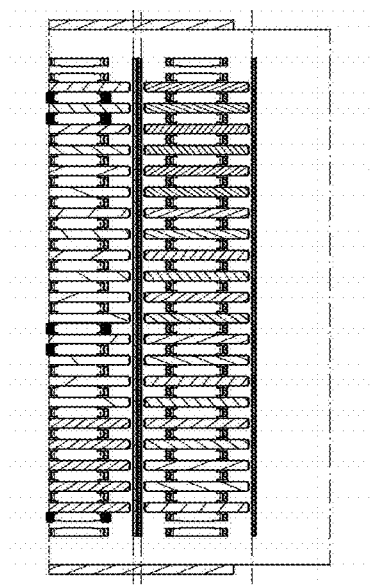
FIG. 14 is a sectional view showing B-B in FIG. 12.

The self-adaptive loading device 21 includes four self-adaptive loading plates for horizontal direction 22 and two self-adaptive floating platforms 23 for upper and lower surfaces; wherein as shown in FIG. 10, the self-adaptive loading plate for horizontal direction 22 includes a fixed plate 401, a sliding plate 402 and a sliding module 403, the sliding module 403 is arranged between the fixed plate 401 and the sliding plate 402, and includes multiple rows of roller chains corresponding to a horizontal displacement;

as shown in FIG. 12, each of the self-adaptive floating platforms 23 for upper and lower surfaces includes a fixed plate 501, an X-direction sliding plate 502, a Y-direction sliding plate 503, an X-direction sliding module 504, a Y-direction sliding module 505 and a reset spring piece 506. The X-direction sliding module 504 is arranged between the fixed plate 501 and the X-direction sliding plate 502, the Y-direction sliding module 505 is arranged between the X-direction sliding plate 502 and the Y-direction sliding plate 503. The X-direction sliding module 504 and the Y-direction sliding module 505 are respectively multiple rows of roller chains which are placed in two orthogonal directions of a horizontal plane.

The three-dimensional loading of the cubic specimen 109 can be divided into loading in the horizontal direction and the vertical direction. Therefore, the self-adaptive loading device 21 is composed of a horizontal self-adaptive loading device and a high-load floating platform.

Figure 11:
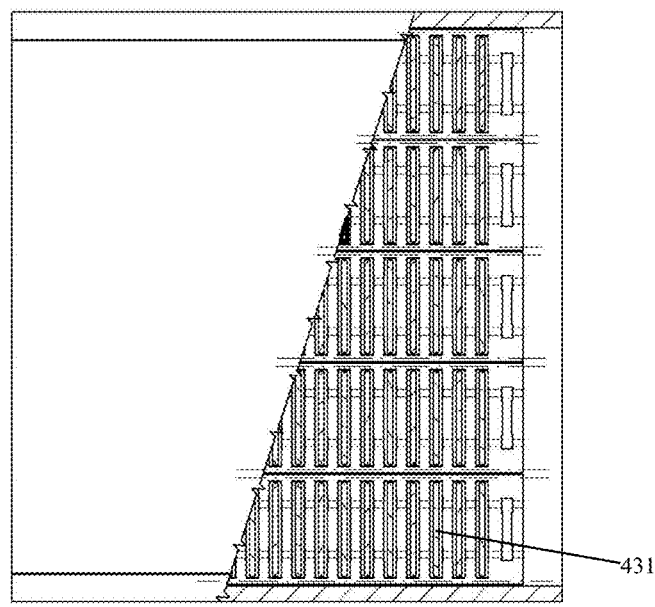
FIG. 11 is a schematic view showing the structure of a sliding module according to the embodiment of the present application.

In order to eliminate the shear stresses in two horizontal directions, a self-adaptive loading plate for horizontal direction 22 is provided to move together with the deformation of the specimen 109. When the specimen 109 is compressed, it is ensured that the pressing head can slide together in a direction in which the specimen 109 may be deformed, and during this process the pressing head can closely fit against the surface of the specimen 109 without relative movement, and can accurately transmit the positive stress provided by a servo cylinder pressing rod to the surface of the specimen 109 at the same time. In this case, the pressing head itself is required to be capable of sliding freely in a direction parallel to the surface of the specimen 109. Therefore, the pressing head is composed of two portions (the fixed plate 401 and the sliding plate 402) which are relatively slidable, and a sliding module (main bearing roller chain 403) with a tiny friction coefficient is arranged between the two portions for connection. Such a mechanism is required to overcome two main problems: first, the sliding module is required to have a bearing capacity above 300 KN, to ensure that deformation or even damage does not occur under a load of 300 KN; second, the friction coefficient can be minimized, to ensure that the pressing head can slide freely along with the specimen 109 under a large positive stress condition. As shown in FIG. 11, a single sliding module is composed of multiple rows of roller chains 431. In order to minimize the friction coefficient, five rows of belt chains each having a length of 150 mm are provided side by side. Each row of the roller chains can bear a dynamic load of 65.2 KN, or a static load of 212 KN, and when the 5 rows of belt chains are used in parallel, a dynamic load can be carried is not less than 300 KN. In this case, a cross-sectional area of only 100×100 mm cannot meet the requirements, therefore the two portions of the sliding module 403 are designed to have different cross-sections, as shown in FIG. 10. The one closely fits against the specimen 109 is a 100×100 mm standard flat pressing plate on which the heating back plate 104 and the pressing plate 103 in the above embodiments are arranged. At a joint with the self-adaptive loading plate for horizontal direction 22, a cross-sectional area of the fixed plate 401 changes into 150×150 mm.

In order to reduce the influence of the shear stress in the vertical direction of the specimen 109, and considering that the deformation at two sides of the specimen 109 may be different in a horizontal loading process, the specimen 109 may be caused to deviate from an original axial center to exceed an action range of the upper and lower pressing plates 103. In order to eliminate shear forces on the upper and lower surfaces of the specimen 109, and ensure that the upper and lower pressing plates 103 can accurately act on the surfaces of the specimen 109, horizontal bidirectional floating platforms, i.e., the self-adaptive floating platforms 23 for upper and lower surfaces are arranged on a bottom support structure and an upper pressing head. The key purpose is to ensure that each of the platforms can move freely in two horizontal directions when being subjected to a load of 500 KN.

The self-adaptive floating platforms 23 for upper and lower surfaces also adopt the sliding modules, but increases the number of the sliding modules arranged on one side as described above to two, and moving directions of the roller chains of the two sliding modules are orthogonal to each other, to ensure that the self-adaptive floating platforms 23 for upper and lower surfaces has degrees of freedom in two directions. FIG. 12 is a schematic view showing a floating platform arranged on a base, wherein an upper protruding portion is a carrying stage 507 of the specimen 109, a lower platform portion is provided with two orthogonal sliding modules (504, 505), and an edge of each of the sliding modules is also provided with a reset spring piece 506. After the external force is unloaded, the reset spring piece 506 may push the upper sliding plates at an upper layer (the X-direction sliding plate 502 or the Y-direction sliding plate 503) back to the initial state with the fixed plate 501, and a same platform having a bidirectional degree of freedom is arranged on the upper pressing head, to ensure the coordinated movement of the upper pressing head with the bottom platform.

Figure 15:
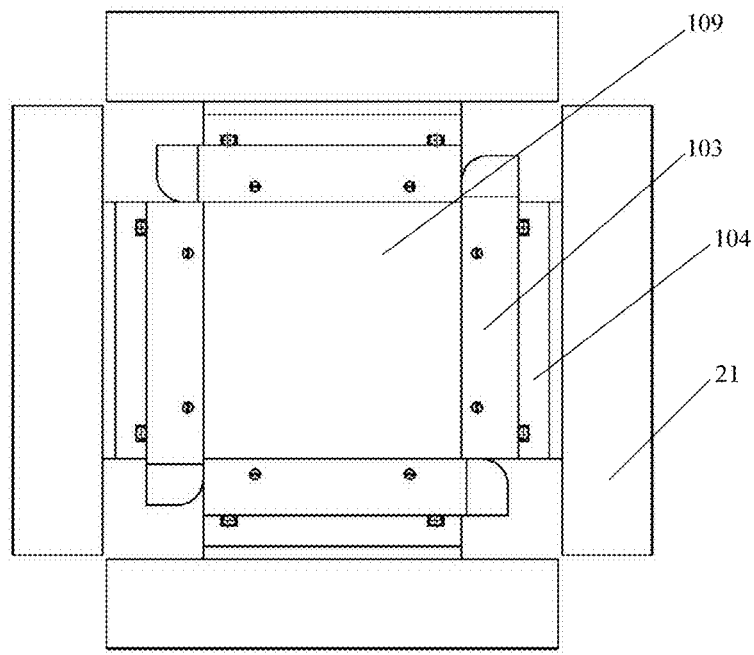
FIG. 15 is a schematic view showing an initial position of the self-adaptive loading device according to the embodiment of the present application.
Figure 16:
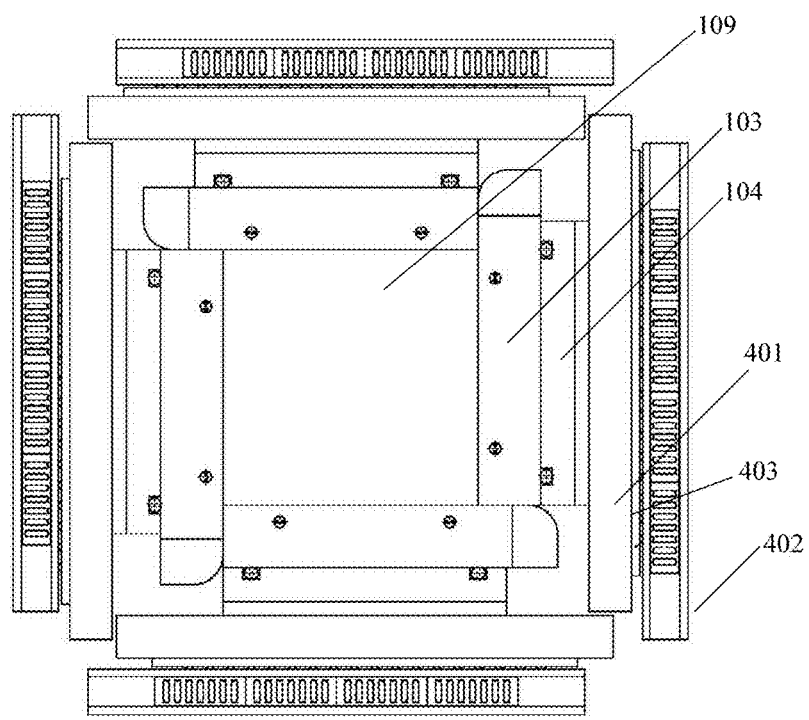
FIG. 16 is a schematic view showing a terminal position of the self-adaptive loading device according to the embodiment of the present application.

A reset spring piece 404 is provided at two ends of the fixed plate 401 and the sliding plate 402, and is configured to push the fixed plate 401 and the sliding plate 402 at two sides back to the initial state after the external load is removed. After the specimen 109 of a cube shape is mounted in position, the self-adaptive loading device 21 closely fits against the four surfaces of the specimen 109 in the horizontal direction, forming a structural form shown in FIG. 15. One side of the fixed plate 401 closely fitting against the specimen 109 extends to act on the adjacent fixed plate 401 in the vertical direction, forming a complete closed loop. In a case that there is a positive stress, the four fixed plates 401 may interact, start to parallelly slide along the respective sliding modules 403, and continuously extrude the specimen 109, to form a final state shown in FIG. 16, so that the specimen 109 reaches the target pressure. During the whole process, there is no relative movement between surfaces of the pressing plates and the surfaces of the specimen 109, and the shear stresses parallel to the surfaces of the specimen 109 are minimized due to the relative sliding of the pressure heads.

In addition, the fracturing fluid pumping system 117 may be a fracturing pumping system for various media of multiple phases, such as various kinds of gases, high temperature and high pressure steam, hydraulic or super-critical phase gas.

Preferably, the fracturing fluid pumping system 117 is a constant temperature and pressure pumping system 117 of supercritical $CO_2$.

Figure 17:
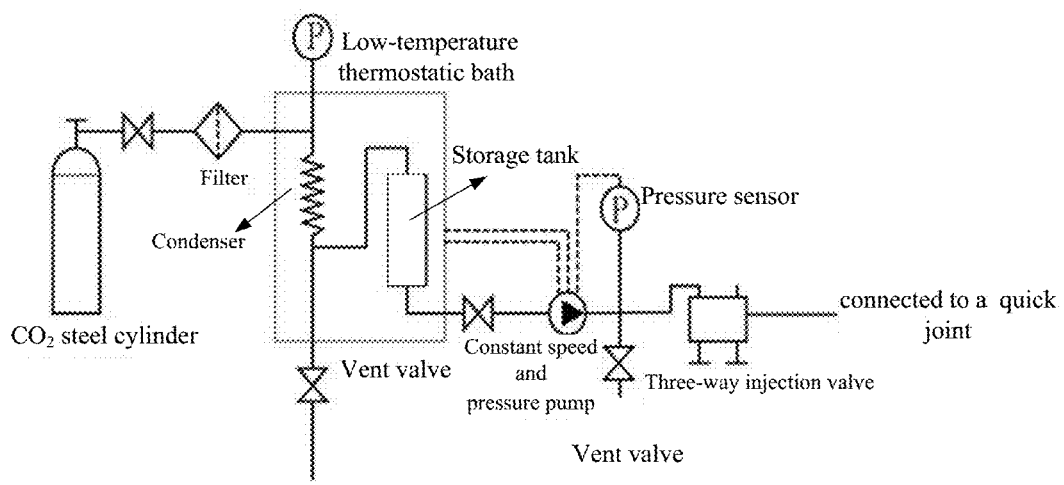
FIG. 17 is a schematic view showing the structure of a constant temperature and pressure pumping system of supercritical $CO_2$ according to the embodiment of the present application.

As shown in FIG. 17, the constant temperature and pressure pumping system 117 of supercritical $CO_2$ includes a $CO_2$ cylinder, a temperature-control thermostatic bath, a constant speed and pressure pump, a three-way injection valve, two vent valves and two pressure sensors; wherein the $CO_2$ cylinder is connected to the temperature-control thermostatic bath through a filter;

the temperature-control thermostatic bath is connected to an input end of the three-way injection valve through the constant speed and pressure pump;

an output end of the three-way injection valve is connected to a quick joint, to function as an output end of the constant temperature and pressure pumping system 117 of supercritical $CO_2$;

the two pressure sensors are arranged in the temperature-control thermostatic bath and the constant speed and pressure pump respectively; and the two vent valves are arranged in the temperature-control thermostatic bath and the constant speed and pressure pump respectively.

The constant temperature and pressure pumping system 117 of supercritical $CO_2$ cooperates with the true triaxial loading system to complete the three-dimensional fracturing experiment. Specifically, the pump is provided with a gas storage tank to connect to an external $CO_2$ steel cylinder, which could fill the gas storage tank with $CO_2$ before each experiment. The pump has a design volume of 250 ml. A servo motor and a programmable controller are employed to cooperate to accurately control the advance, retreat, speed regulation and pressure regulation of the pump, etc., thus achieving a working pressure of 0-70 MPa, and an output pressure curve can be used to display real-time changes of flow rate, flow quantity and pressure of the liquid. In addition, considering the injection of the supercritical $CO_2$, can $CO_2$ reach the supercritical state only when the temperature reaches 31.06° C. and the pressure reaches 7.38 MPa. The pressure condition can be achieved by pushing a piston to raise the pressure of $CO_2$ in a chamber. In order to achieve the corresponding temperature condition, the pump is equipped with a low temperature thermostat system to ensure that the temperature can be varied within the range of −5 to 100° C. Meanwhile an over-temperature protection is also provided to automatically cut off the electric heating system to ensure the safety of apparatus when the temperature exceeds a limit temperature.

Compared with the hydraulic fracturing technology, related studies show that supercritical $CO_2$ fracturing can increase the complexity of the fracturing crack network. Therefore, in order to reveal the mechanism of crack initiation and propagation of the fracturing crack network, it is necessary to accurately grasp and understand the evolution law of global stress field during complex crack network initiation and propagation process.

By studies, the applicant incorporates the 3D printing, the stress-freezing technology and the supercritical $CO_2$ constant temperature and pressure output, and then applies them to quantitative and visualization characterization of the three-dimensional stress field inside rocks having complex cracks, thus the evolution law of the stress field during the supercritical $CO_2$ fracturing process can be accurately grasped and quantitatively characterized. This method finds a new way to visually observe and transparently display the distribution and evolution law of the three-dimensional stress field inside complex solid structures using physical model experimental method, and meanwhile it provides a new approach to verify the accuracy of numerical simulation analyses of the three-dimensional stress field inside the complex solid structures.

The specific operation principle is the same as that of the above embodiment, and will not be described herein.

The above embodiments in this specification are described in a progressive manner. Each of the embodiments is mainly focused on describing its differences from other embodiments, and references may be made among these embodiments with respect to the same or similar portions among these embodiments. For the device provided in the embodiments, since it corresponds to the method provided in the embodiments, the description is relatively simple, and the related parts may refer to the description of the method.

The embodiments described hereinabove are only preferred embodiments of the present application, and are not intended to limit the scope of the present application in any form. Although the present application is disclosed by the above preferred embodiments, the preferred embodiments should not be interpreted as a limitation to the present application. For those skilled in the art, many variations, modifications or equivalent replacements may be made to the technical solutions of the present application by using the methods and technical contents disclosed hereinabove, without departing from the scope of the technical solutions of the present application. Therefore, any simple modifications, equivalent replacements and modifications, made to the above embodiments based on the technical essences of the present application without departing from the technical solutions of the present application, are deemed to fall into the scope of the technical solution of the present application.

What is claimed is:

1. A device for stress-freezing experiments during fracturing process, comprising:

a temperature control system, which comprises a thermo-controlled oven and is configured to perform heating and cooling treatment on a specimen arranged in the thermo-controlled oven according to a preset temperature gradient and a photosensitive curve, to realize stress-freezing experiment to the specimen, wherein the specimen is a transparent photosensitive model printed by a 3D printer, and the photosensitive curve is a photosensitive curve of the photosensitive model;

a true triaxial servo loading system configured to apply a pressure to the specimen; and a fracturing fluid pumping system having an output end arranged in the thermo-controlled oven and being configured to perform a corresponding fracturing experiment to the specimen; and wherein, the device for stress-freezing experiments during fracturing process further comprises a self-adaptive loading device arranged between the heating back plates and the piston rods, wherein the self-adaptive loading device is in contact with the piston rods, and is configured to eliminate shear stresses on surfaces of the specimen; and wherein, the self-adaptive loading device comprises four self-adaptive loading plates for horizontal direction and two self-adaptive floating platforms for upper and lower surfaces;

a horizontal assembly comprises a fixed plate, a sliding plate and a sliding module, the sliding module is arranged between the fixed plate and the sliding plate and comprises a plurality of rows of roller chains corresponding to a horizontal displacement; and an upper and lower direction assembly comprises a fixed plate, two sliding plates and two sliding modules, wherein one sliding module is arranged between the fixed plate and one sliding plate and another sliding module is arranged between the two sliding plates, and the two sliding modules are respectively a plurality of rows of roller chains which are placed in two orthometric directions of a horizontal plane.

2. The device for stress-freezing experiments during fracturing process according to claim 1, wherein the thermo-controlled oven comprises a multi-hole cover plate, a sealing assembly and five thermo-controlled oven walls; wherein
the multi-hole cover plate and the five thermo-controlled oven walls are each provided with a piston rod inlet; and
the multi-hole cover plate is provided with two circulating air inlets.

3. The device for stress-freezing experiments during fracturing process according to claim 1, wherein the temperature control system further comprises a heat source control system, a direct heating unit, an ambient heating unit, a cooling control system, a cooling unit and a temperature detecting unit; wherein
the heat source control system is configured to control the operations of the direct heating unit and the ambient heating unit; and
the cooling control system is configured to control the operation of the cooling unit.

4. The device for stress-freezing experiments during fracturing process according to claim 3, wherein
the direct heating unit comprises six electric heating tubes and six heating back plates;
the ambient heating unit comprises an air heater;
the cooling unit comprises six cooling tubes;
the temperature detecting unit comprises at least six temperature sensors;
each of the electric heating tubes is arranged in the respective heating back plate, to perform main temperature rising treatment in various directions of the specimen through direct heating or directly cool the specimen by injecting a cooling liquid;
the air heater is configured to perform temperature rising compensation to the specimen by increasing an ambient temperature;
the temperature sensors are respectively arranged in the thermo-controlled oven and pressing plates of the true triaxial servo loading system;
one side of each of the heating back plates is connected to a self-adaptive loading device, and another side of each of the heating back plates is attached to one of the pressing plates;
the cooling control system is configured to control the injection of the cooling liquid or a cooling gas in the cooling tubes; and
each of the cooling tubes is arranged at an inner side of the thermo-controlled oven wall.

5. The device for stress-freezing experiments during fracturing process according to claim 1, wherein the true triaxial servo loading system comprises beam and column frames, five sets of servo actuators, five sets of servo distributors, a set of servo oil source, a set of servo motion control system, hydraulic system accessories, a self-adaptive series stress sensor, a displacement sensor and a specimen fixing and positioning unit; wherein
the specimen fixing and positioning unit is arranged at a bottom of the thermo-controlled oven;
the beam and column frames are configured to support piston rods, the multi-hole cover plate and the specimen fixing and positioning unit and to allow the same to realize controllable movement;
the output of the servo motion control system controls the corresponding servo actuator to move through the respective servo distributor;

the five sets of servo actuators apply pressure on a top of the specimen and in horizontal directions of the specimen by corresponding piston rods and pressing plates respectively;
the servo oil source and the hydraulic system accessories are used to push the corresponding piston rods by the five sets of servo actuators;
the self-adaptive series stress sensor is configured to measure stresses applied to the specimen in various directions; and
the displacement sensor is configured to measure displacements of the specimen in various directions.

6. The device for stress-freezing experiments during fracturing process according to claim 5, wherein the self-adaptive series stress sensor comprises a large-range pressure sensor, a small-range pressure sensor, a mounting sleeve, a thrust plate and an elastomer; wherein
the small-range pressure sensor is arranged in the mounting sleeve;
the elastomer is arranged between a bottom of the mounting sleeve and the small-range pressure sensor;
a deformation gap of the elastomer is set between the thrust plate and a top of the mounting sleeve;
the small-range pressure sensor is configured to detect a pressure applied by the thrust plate; and
the large-range pressure sensor is configured to detect a pressure applied by the mounting sleeve.

7. The device for stress-freezing experiments during fracturing process according to claim 1, further comprising a specimen automatic fixing and positioning unit, wherein the specimen automatic fixing and positioning unit comprises four orienting guide rails, a specimen mounting platform, a fixture and a top servo actuator;
the specimen mounting platform slides along the four orienting guide rails, and moves in linkage with the top servo actuator to achieve the lifting mounting and accurate positioning of the specimen.

8. The device for stress-freezing experiments during fracturing process according to claim 1, wherein the fracturing fluid pumping system is a constant temperature and pressure pumping system of supercritical $CO_2$.

9. The device for stress-freezing experiments during fracturing process according to claim 1, wherein
the constant temperature and pressure pumping system of supercritical $CO_2$ comprises a $CO_2$ cylinder, a temperature-control thermostatic bath, a constant speed and pressure pump, a three-way injection valve, two vent valves and two pressure sensors; wherein
the $CO_2$ cylinder is connected to the temperature-control thermostatic bath through a filter;
the temperature-control thermostatic bath is connected to an input end of the three-way injection valve through the constant speed and pressure pump;
an output end of the three-way injection valve is connected to a quick joint, to function as an output end of the constant temperature and pressure pumping system of supercritical $CO_2$;
the two pressure sensors are arranged in the temperature-control thermostatic bath and the constant speed and pressure pump respectively; and
the two vent valves are arranged in the temperature-control thermostatic bath and the constant speed and pressure pump respectively.

* * * * *